United States Patent
Petrinic et al.

(10) Patent No.: US 7,409,848 B2
(45) Date of Patent: Aug. 12, 2008

(54) APPARATUS AND METHOD FOR BULGE TESTING AN ARTICLE

(75) Inventors: Nikica Petrinic, Oxford (GB); Carlos Ruiz, Oxford (GB)

(73) Assignee: Rolls-Royce plc, London (GB)

( * ) Notice: Subject to any disclaimer, the term of this patent is extended or adjusted under 35 U.S.C. 154(b) by 0 days.

(21) Appl. No.: 11/723,293

(22) Filed: Mar. 19, 2007

(65) Prior Publication Data

US 2007/0220966 A1     Sep. 27, 2007

Related U.S. Application Data

(63) Continuation of application No. 11/132,245, filed on May 19, 2005, now abandoned.

(30) Foreign Application Priority Data

Jun. 18, 2004    (GB)   ................................ 0413650.3

(51) Int. Cl.
     *G01M 7/08*      (2006.01)
     *G01B 21/20*      (2006.01)
(52) U.S. Cl. .................. 73/12.08; 73/12.11; 73/150 A
(58) Field of Classification Search ................ 73/12.11, 73/12.08
See application file for complete search history.

(56) References Cited

U.S. PATENT DOCUMENTS 2,696,105 A * 12/1954 Mackas ...................... 73/12.08

(Continued)

FOREIGN PATENT DOCUMENTS

SU      1453 231    *    1/1989

OTHER PUBLICATIONS

Alaca B E, Selby J C, Saif M T A, Sehitoglu H. 2002. Biaxial testing of nanoscale films on compliant substrates: Fatigue and fracture. Review of Scientific Instruments 73 pp. 2963-2965. Accessed online on Sep. 18, 2006. http://home.ku.edu.tr/~ealaca/pdf/Publications/RSI_Aug02.pdf.*

(Continued)

*Primary Examiner*—Edward Lefkowitz
*Assistant Examiner*—Punam Patel
(74) *Attorney, Agent, or Firm*—W. Warren Taltavull; Manelli Denison & Selter PLLC (57) ABSTRACT

An apparatus (10) for bulge testing an article (12) comprises a pressure vessel (14) arranged to define a chamber (15), the pressure vessel (14) has a first aperture (28) and a second aperture (30), means to pressurize the chamber (15), means (19) to measure the deflection of the article (12, means (39) to measure the pressure in the pressure vessel (14) and means (18) to determine material properties of the article (12) using the measurements of pressure in the pressure vessel (12) and the measurements of deflection of the article (12). A piston (24) is arranged to move within the pressure vessel (14) and the chamber (15) is filled with a fluid. The means to pressurise the pressure vessel (14) comprises a gun (16) arranged to fire a projectile (36) to strike the piston (24) to produce a high pressure in the fluid in the chamber (15) in the pressure vessel (14) to deform an article (12) placed over the first aperture (28) in the pressure vessel (14) to seal the pressure vessel (14). The means (19) to measure deflection comprises a camera 48 and two mirrors (50,52) to produce a stereoscopic view of the article (10).

28 Claims, 5 Drawing Sheets

U.S. PATENT DOCUMENTS

| | | | |
|---|---|---|---|
| 3,074,170 A * | 1/1963 | Zabel et al. | 33/228 |
| 3,109,057 A * | 10/1963 | Campanella et al. | 348/46 |
| 3,277,693 A * | 10/1966 | D Amato et al. | 73/12.09 |
| 3,729,980 A * | 5/1973 | Johnson et al. | 73/12.08 |
| 4,234,241 A * | 11/1980 | Schmidt | 359/220 |
| 4,483,190 A * | 11/1984 | Cornett | 73/167 |
| 4,735,092 A * | 4/1988 | Kenny | 73/840 |
| 4,905,502 A * | 3/1990 | Gram | 73/49.4 |
| 5,311,856 A * | 5/1994 | White et al. | 124/56 |
| 6,050,138 A * | 4/2000 | Lynch et al. | 73/150 A |
| 6,539,790 B2 * | 4/2003 | Huston et al. | 73/150 A |
| 6,603,876 B1 * | 8/2003 | Matsuo et al. | 382/154 |
| 2004/0261494 A1 * | 12/2004 | Lee | 73/12.09 |
| 2005/0094853 A1 * | 5/2005 | Kang | 382/111 |

OTHER PUBLICATIONS

Bourne N K. 2003. A 50mm bore gas gun for dynamic loading of materials and structures. Meas. Sci. Technol. 14 273-8. Accessed online on Sep. 18, 2006. http://ej.iop.org/links/rt5c23MIE/1A5sGxxH2xGhIBvPav5vpA/e30304.pd.*

* cited by examiner

Best Fit

APPARATUS AND METHOD FOR BULGE TESTING AN ARTICLE

This application is a Continuation of National Application Number 11/132,245 filed May 19, 2005.

FIELD OF THE INVENTION

The present invention relates to an apparatus and method for bulge testing an article.

BACKGROUND OF THE INVENTION

Conventional apparatus for bulge testing an article comprises a pressure vessel arranged to define a chamber and in use the article being arranged over an aperture in the pressure vessel to seal the pressure vessel. A source of pressurised fluid is arranged to supply fluid to the chamber to cause the article to deform or bulge. Means to measure the material properties of the article are provided by measuring the pressure of the fluid supplied to the chamber and the deflection of the article.

U.S. Pat. No. 4,735,092 provides a micrometer to measure the vertical displacement of the article when the article has been deformed and the tensile strength of the article is calculated.

WO02/47372A provides a Michelson interferometer that generates an interference pattern having fringes and nodes that move when the article has been deformed and the material properties of the article are calculated.

SUMMARY OF THE INVENTION

Accordingly the present invention seeks to provide a novel apparatus and a novel method for bulge testing an article.

Accordingly the present invention provides an apparatus for bulge testing an article comprising a pressure vessel arranged to define a chamber, the pressure vessel having a first aperture and a second aperture, means to pressurise the chamber, means to measure the deflection of the article, means to measure the pressure in the pressure vessel and means to determine material properties of the article using the measurements of pressure in the pressure vessel and the measurements of deflection of the article, a piston being arranged to move within the pressure vessel, the chamber being filled with a fluid, the means to pressurise the pressure vessel comprising a gun arranged to fire a projectile to strike the piston to produce a high pressure in the fluid in the chamber in the pressure vessel to deform the article, whereby in use the article being arranged over the first aperture in the pressure vessel to seal the pressure vessel.

Preferably the apparatus comprises a clamping member having an aperture, the clamping member being arranged in use such that the aperture in the clamping member is aligned with the first aperture in the first end of the pressure vessel to clamp the article between the first end of the pressure vessel and the clamping member such that the article extends across the first aperture in the first end of the pressure vessel to seal the first end of the pressure vessel, Preferably the piston being arranged to seal the second end of the pressure vessel.

Preferably the gun including a barrel and a projectile arranged to move within the barrel, the end of the barrel being secured to the second end of the pressure vessel and the second aperture in the second end of the pressure vessel being aligned with the barrel such that in use the projectile may strike the piston to produce a high pressure in the fluid in the pressure vessel to deform the article.

Preferably the pressure vessel has a minimum cross-sectional area at a position between the first end and the second end.

Preferably the gun is a gas gun. The gun may be an electromagnetic gun or a percussive gun.

Preferably the pressure vessel contains a liquid, more preferably the pressure vessel contains an oil.

Preferably the means to measure the pressure comprises a high-speed high pressure gauge.

Preferably there are means to measure the velocity of the projectile before impact with the piston.

Preferably the means to measure the velocity comprises a plurality of light beams spaced apart along the length of the barrel, each light beam extends transversely across the barrel.

Preferably the means to measure the deflection of the article comprises at least one high-speed high-resolution camera.

The means to measure the deflection of the article may comprise two high-speed high-resolution cameras arranged to produce a stereoscopic view of the article.

Preferably the means to measure the deflection of the article comprises two mirrors arranged at different angles relative to the surface of the article to produce a stereoscopic view of the article, each mirror being arranged to focus on a portion of the image plane of the camera.

Preferably a first mirror is arranged at a predetermined angle and the angle of a second mirror is adjustable.

Preferably the first mirror is arranged at an angle of 45°.

Preferably the means to measure the material properties of the article comprises a processor to analyse the stereoscopic view of the article.

Preferably the processor has means to determine the angle of the second mirror relative to the undeformed article.

Preferably the processor has means to determine the altitude of a polar point on the deformed article relative to the undeformed article from the determined angle of the second mirror.

Preferably the processor has means to determine the altitude of other points on the deformed article relative to the undeformed article from the determined angle for the second mirror.

Preferably the processor determines the chord length, the dome segment height and the radius of the deformed article between a pair of dots arranged symmetrically about the pole point of the deformed article.

Preferably the processor determined the chord length, the dome segment height and the radius of the deformed article between a plurality of pairs of dots, each pair of dots is arranged symmetrically about the pole point of the deformed article.

Preferably the processor determines the chord length, the dome segment height and the radius of the deformed article at a plurality of times during the deformation of the article.

Preferably the means to determine material properties of the article determines the thickness of the deformed article from the chord length and dome height of the deformed article.

Preferably the means to determine material properties of the article determines the stress in the deformed article from the pressure applied and the original thickness of the article and the radius of the deformed article.

The present invention also provides a method of bulge testing an article comprising providing a pressure vessel arranged to define a chamber, the pressure vessel having a first aperture and a second aperture, a piston being arranged to move within the pressure vessel, the chamber being filled with a fluid, arranging the article over the first aperture in the pressure vessel to seal the pressure vessel, firing a projectile to strike the piston to produce a high pressure in the fluid in the chamber in the pressure vessel to deform the article, measuring the deflection of the article, measuring the pressure in the pressure vessel and determining material properties of the article using the measurements of pressure in the pressure vessel and the measurements of deflection of the article.

The present invention also provides an apparatus for bulge testing an article comprising a pressure vessel arranged to define a chamber, the pressure vessel having a first aperture, means to pressurise the chamber, means to measure the deflection of the article, means to measure the pressure in the pressure vessel and means to determine material properties of the article using the measurements of pressure in the pressure vessel and the measurements of deflection of the article, wherein the means to measure the deflection of the article comprising two mirrors arranged at different angles relative to the surface of the article to produce a stereoscopic view of the article, each mirror being arranged to focus on a portion of the image plane of a camera.

The present invention also provides a method of bulge testing an article comprising providing a pressure vessel arranged to define a chamber, the pressure vessel having a first aperture, arranging the article over the first aperture in the pressure vessel to seal the pressure vessel, pressurising the chamber in the pressure vessel to deform the article, measuring the deflection of the article, measuring the pressure in the pressure vessel and determining material properties of the article using the measurements of pressure in the pressure vessel and the measurements of deflection of the article, wherein the measuring of the deflection of the article comprising providing two mirrors arranged at different angles relative to the surface of the article to produce a stereoscopic view of the article and arranging each mirror to focus on a portion of the image plane of a camera.

BRIEF DESCRIPTION OF THE DRAWINGS

The present invention will be more fully described by way of example with reference to the accompanying drawings in which.

DETAILED DESCRIPTION OF THE INVENTION

An apparatus 10 for bulge testing an article 12 according to the present invention is shown in FIGS. 1 to 5 and comprises a fluid filled pressure vessel 14, a gun 16, means 19 to measure deflection of the article 12, means 39 to measure pressure in the pressure vessel 14 and means 18 to determine the material properties of the article 12. The pressure vessel 14 has a first end 20, a second end 22, a piston 24 arranged to move within the pressure vessel 14 and a clamping member 26. The first end 20 of the pressure vessel 14 has a first aperture 28 and the second end 22 of the pressure vessel 14 has a second aperture 30. The clamping member 26 has an aperture 32 and the clamping member 26 is arranged in use such that the aperture 32 in the clamping member 26 is aligned with the first aperture 28 in the first end 20 of the pressure vessel 14 to clamp the article 12 between the first end 20 of the pressure vessel 14 and the clamping member 26 such that the article 12 extends across the first aperture 28 in the first end 20 of the pressure vessel 14 to seal the first end 20 of the pressure vessel 14. The piston 24 is arranged to seal the second end 22 of the pressure vessel 14. The pressure vessel 14 has a minimum cross-sectional area 38 at a position between the first end 20 and the second end 22. The pressure vessel 14 preferably defines a chamber 15, which is circular in cross-section, but the chamber 15 may be triangular, rectangular, square, elliptical or other suitable shapes may be used. The first aperture 28 and second aperture 30 in the pressure vessel 14 have the same cross-sectional shape as the chamber 15 in the pressure vessel 14.

Figure 1:
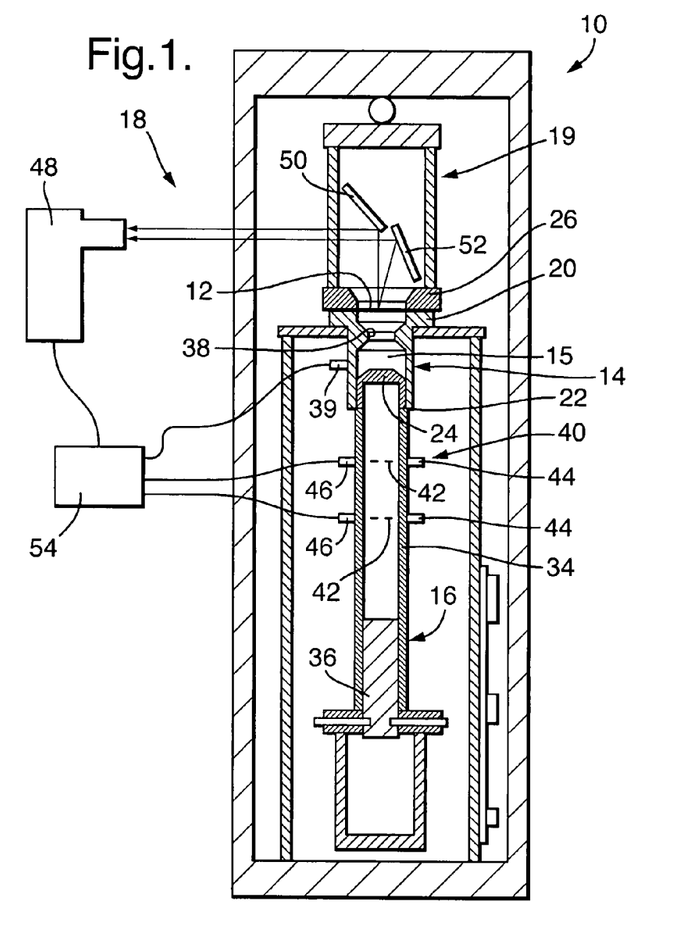
FIG. 1 shows a schematic longitudinal cross-sectional view through an apparatus for bulge testing an article according to the present invention.

The gun 16 includes a barrel 34 and a projectile 36 is arranged to move within the barrel 34. The end of the barrel 34 is secured to the second end 22 of the pressure vessel 14 and the second aperture 30 in the second end 22 of the pressure vessel 14 is aligned with the barrel 34. The gun 16 is preferably a gas gun, but the gun 16 may be an electromagnetic gun or a percussive gun or other suitable gun capable of firing the projectile 36 at velocities of up to 40 $ms^{-1}$.

The chamber 15 of the pressure vessel 14 contains a liquid, for example the pressure vessel 14 contains an oil.

The pressure vessel 14 is provided with means 39 to measure the pressure in the pressure vessel 14. The means 39 to measure the pressure comprises a high-speed high pressure gauge. The means 39 to measure the pressure is arranged to supply signals to a processor 54.

The gun 16 is provided with means 40 to measure the velocity of the projectile 36 before the projectile 36 impacts with the piston 24. Preferably the means 40 to measure the velocity of the projectile 36 comprises a plurality of light beams 42 spaced apart along the length of the barrel 34, each light beam 42 extends transversely across the barrel 34. The light beams 42 are produced by light sources 44 and the light beams 42 are detected by light detectors 46. The light detectors 46 supply signals to the processor 54. The breaking of a first light beam 42 starts a clock and the breaking of the second light beam 42 stops the clock and the velocity of the projectile 36 is determined from the time taken to travel between the two light beams 42 and the known distance between the light beams 42, which is calculated in the processor 54.

The means 19 to measure the deflection of the article 12 comprises at least one high-speed high-resolution camera 48, two mirrors 50 and 52 and the processor 54. The high-speed high-resolution camera 48 may be used at rates at or between 11000 and 22000 frames per second. The high-speed high-resolution camera 48 uses high-resolution photographic films, which are digitised before image analysis is performed. Each recorded image contains information about the deformation, displacement, of points, dots, on the article 12 as a function of time. The two mirrors 50 and 52 are arranged at different angles to produce a stereoscopic view of the article 12, each mirror 50 and 52 respectively is arranged to focus on a portion, half, of the image plane of the camera 48. A first mirror 50 is arranged at a predetermined angle and the angle of a second mirror 52 is adjustable. The first mirror 50 is arranged at an angle of 45° to the surface of the undeformed article 12.

The processor 54 is arranged to analyse the stereoscopic view of the article 12 produced by the camera 48 to determine the deflection of the article 12.

Figure 5:
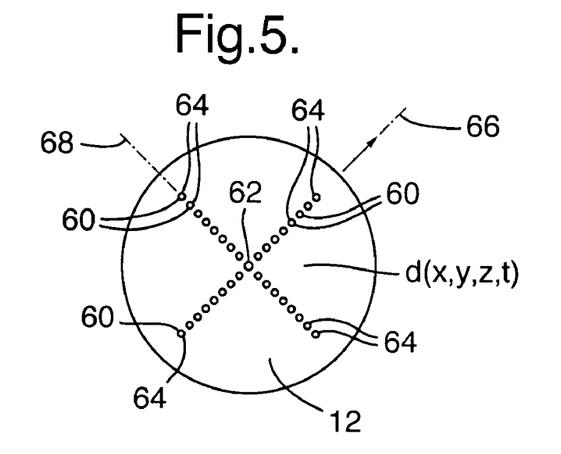
FIG. 5 is a view in the direction of arrow B in FIG. 4.

The article 12 for dynamic bulge testing is initially marked with a regular grid, for example a rectangular grid, of dots 60 in order to enable the calculation of surface displacement of the article 12 during the deformation process from the photographic images produced by the high speed high resolution camera 48, see FIG. 5.

Figure 2:
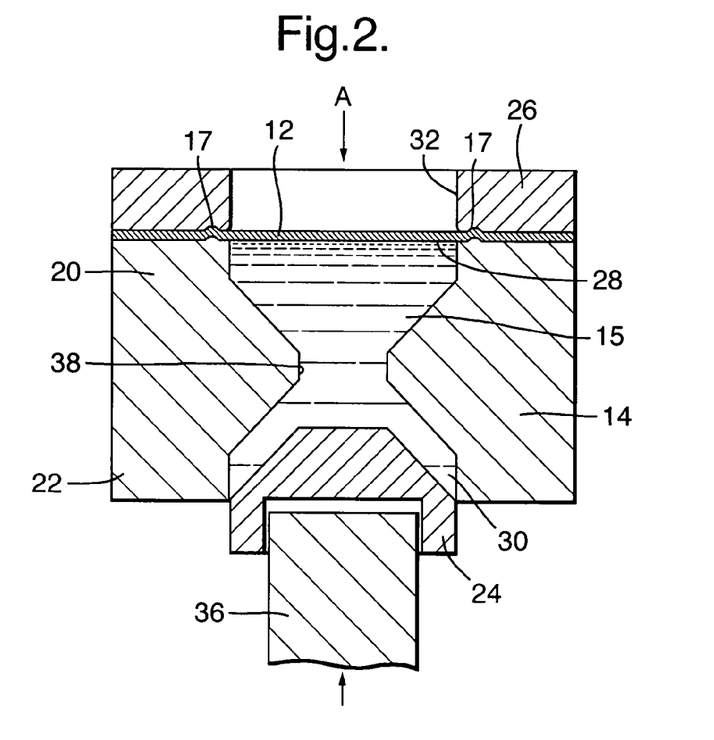
FIG. 2 is a schematic enlarged longitudinal cross-sectional view of part of the apparatus shown in FIG. 1.
Figure 3:
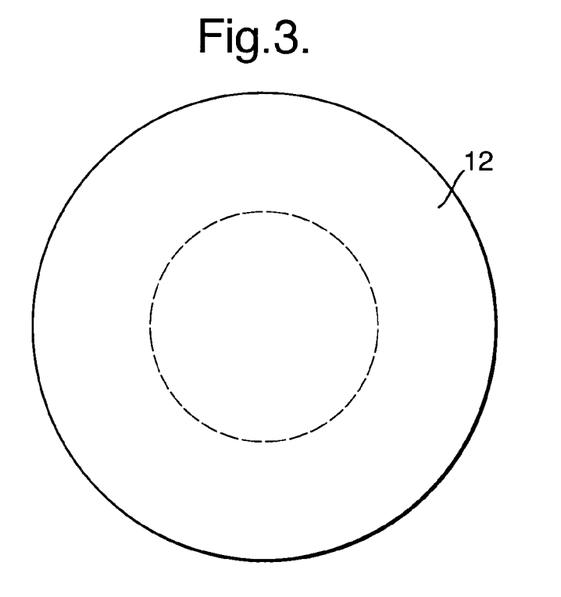
FIG. 3 is a view in the direction of arrow A in FIG. 2.

The article 12 is placed between the first end 20 of the pressure vessel 14 and the clamping member 26 and the clamping of the article 12 deforms the article 12 near draw beads 17 but leaves the article 12 unaffected within the aperture 28. The draw beads 17 are positioned as close as possible to the inner diameter of the pressure vessel 14 to prevent material being drawn into the pressure vessel 14 during loading. Excess oil is forced out of the pressure vessel 14 during deformation of the article 12 along the draw bead 17 allowing the article 12 to seal the pressure vessel 14 without trapping any gas, air.

Figure 4:
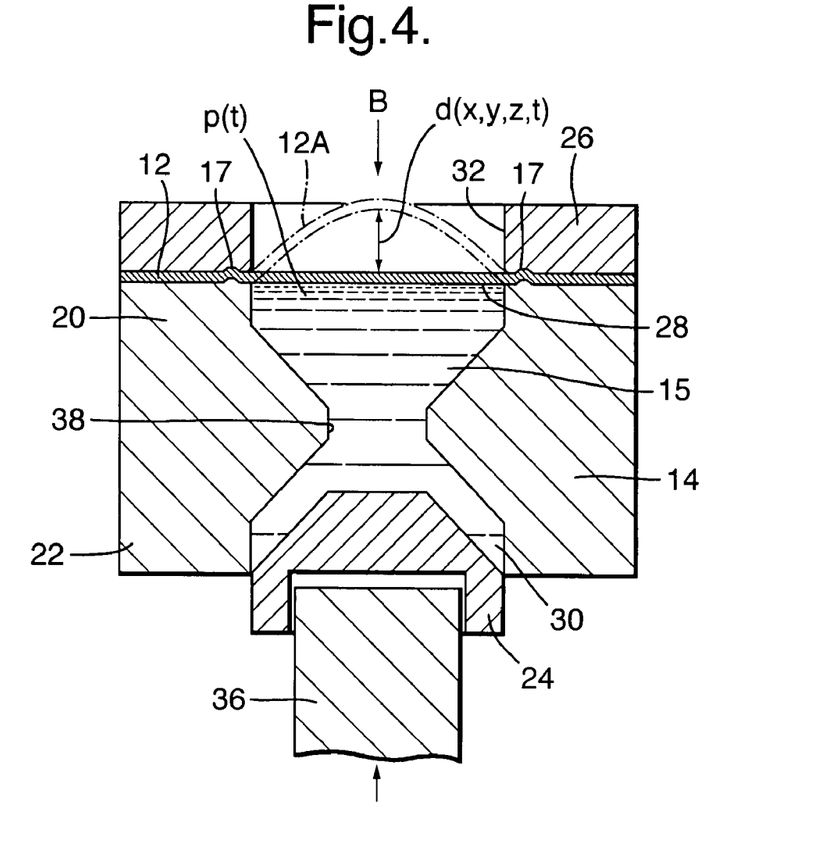
FIG. 4 is an alternative schematic enlarged longitudinal cross-sectional view of part of the apparatus shown in FIG. 1.

In use the gun 16 is fired and the projectile 36 travels along the barrel 34 and strikes the piston 24. The piston 24 moves within the pressure vessel 14 and compresses the fluid, oil, in the chamber 15 to produce a high pressure in the fluid in the pressure vessel 14 to rapidly deform the article 12 to the position 12A, as shown in FIG. 4.

Any data measured during the dynamic bulge testing is recorded in the processor 54 using a computer controlled multi-channel data acquisition system capable of recording data rates of up to 20 $MSs^{-1}$ (Mega-Samples per second). The data acquisition is performed at 500 $kSs^{-1}$ (kilo-Samples per second). During the dynamic bulge testing the total pressure applied in the pressure vessel 14 as a function of time was measured by the means 39 to measure the pressure in the pressure vessel 14 and the surface displacements of the article 12 as a function of time are measured by the high speed high resolution camera 48 using the grid of dots 60 on the article 12. The data obtained is in the form of analogue electric signals from the means 39 to measure pressure and analogue images from the camera 48. These signals may be digitised before going to the processor 54 or by the processor 54.

The pressure signals recorded during the dynamic bulge testing are often masked by high frequency noise, due to electronic noise and pressure waves in the complex geometry of the pressure vessel 14 which interfere. In order to eliminate the undesired noise the pressure signal is filtered using a FFT (Fast Fourier Transform) in which the pressure signals are converted to their frequency spectrum using FFT after which the high frequencies are subtracted and the pressure signals are converted back using Inverse FFT.

Figure 6:
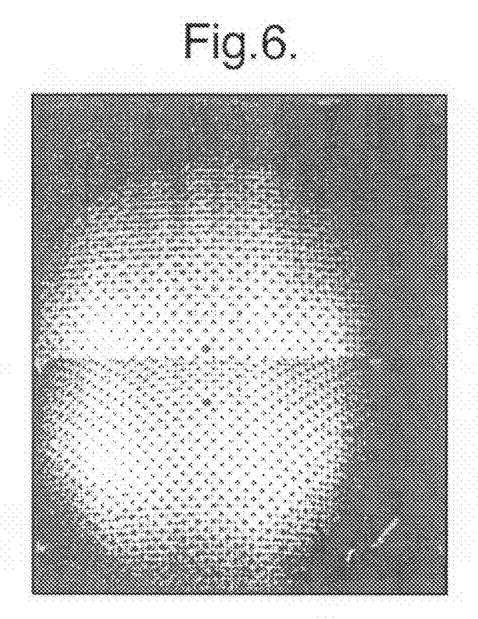
FIG. 6 is a view of an original image.

The images of the article 12 captured by the camera 48 during deformation of the article 12 are analysed as follows. The analysis starts by considering an "original image" of the undeformed article 12, see FIG. 6. The first step of the analysis is to determine the "local background" of the "original image" by median filtering on an N×N mask (for example N=25, but may vary between 15 and 25 depending on image quality). The "local background" is subtracted from the "original image" to leave the desired features, the dots 60. The image is also inverted and the range is adjusted to make it suitable for further analysis.

In the nest step the image is converted to black and white using a simple threshold procedure, the threshold value is optimally adjusted to give the best results. Then "speckle noise" is removed with a 2×2 median filter.

Then each feature, dot, 60 is labelled. In this example the dots 60 are coloured in different shades for clarity. After the dots 60 are labelled it is possible to calculate the centroids and surface area, count the number of pixels, of each dot 60.

In the next step the location, the coordinates, of the polar point 62 in the two images of the article 12 is determined, it is assumed that the polar point 62 is represented by the largest coloured area in each of the two images. The location of the polar point 62 in the two images is used to locate the coordinates of the dots 60 in the grid. Some error checking may be used that each dot 60 is not too far from its expected location and that there are no repeated dots 60. The dots 60 detected from the first mirror 50 arranged at 45° are centre point superimposed on the original image and the dots 60 detected from the second mirror 52 are superimposed on the original image. The obtained results are superimposed over the original images during image analysis to enable simple visual control. The image analysis procedure completes with an output of the dot 60 coordinates into suitable files, one file for the entire dot field and one for the principal meridians only.

The change in coordinates of the marked dots 60 on the surface of the article 12 during dynamic bulge testing provides the necessary information about the deformation of the article 12. This holds the key to determining the strains and combined with the pressure signals provided by the means 18 to measure pressure the key to determining the stress at the polar point 62 of the article 12. The polar point 62 is the centre point of the article 12, e.g. is in the centre of the first aperture 28.

Figure 7:
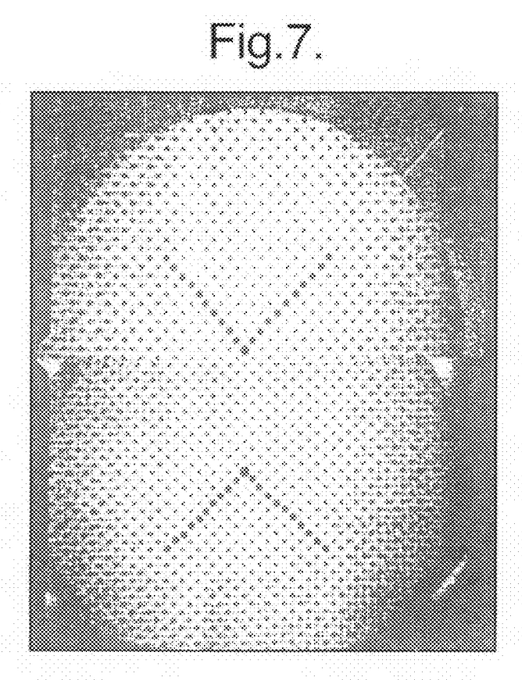
FIG. 7 is a view of an image with principal meridians marked.

In one particular example only the dots 64 marked along primary perpendicular meridians 66 and 68 intersecting the polar point 62 are used, and only 10 dots in each primary meridian 66 and 68 excluding the polar point 62, see FIGS. 5 and 7. It may be possible to use other selections of dots 60.

Initially the angle φ of the second mirror 52 relative to the original surface of the article 12 is determined. The angle of the second mirror 52 is obtained by examining the distance "a" between two points on the surface, plane, of the article 12 and the distance "a'" between the corresponding two points on the image plane.

Thus $\sin(180-2\phi)=a'/a$ $\phi=\frac{1}{2}\arcsin(a'/a)=90°-\frac{1}{2}\arcsin(a'/a)$ The altitude, or height, or z coordinate of the polar point 62 is determined. The height of the polar point 62 is determined using the second mirror 52. At each stage during bulging the position of the polar point 62 is compared to its initial position when the article 12 is undeformed and is flat. The height of the bulge $z_p$ is calculated from trigonometric descriptions of triangles 1 and 2 in FIG. 8.

Figure 8:
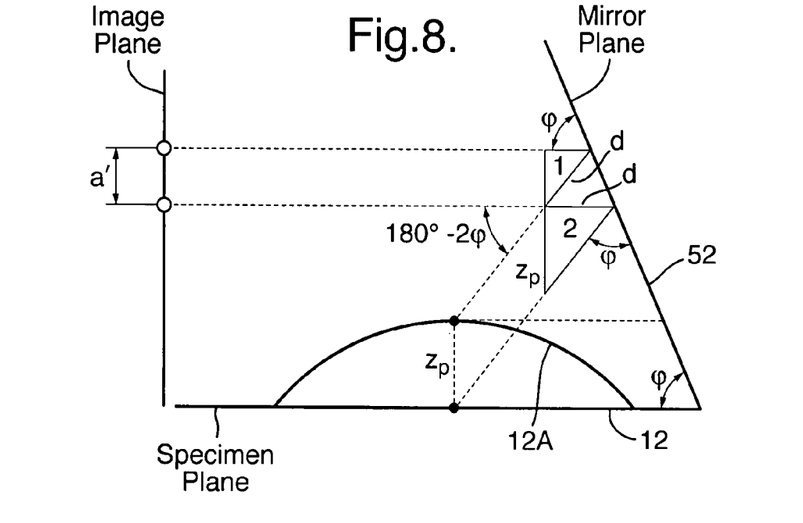
FIG. 8 is a chart showing calculation of deflection of polar point of deformed article.

$\sin(180°-2\phi)=a'/d$ for triangle 1

$\tan(180°-2\phi)=z_p/d$ for triangle 2 thus $z_p=-a'/\cos(2\phi)$

Figure 9:
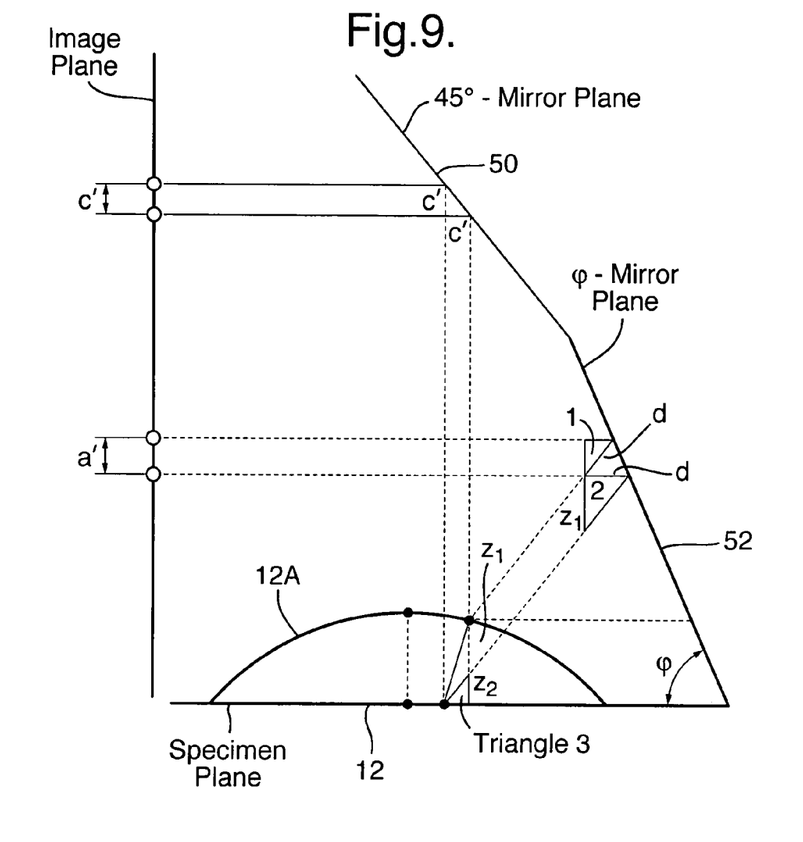
FIG. 9 is a chart showing calculation of deflection of other points of deformed article.

The altitude, or height, or z coordinate of the dots 64 along the primary meridians 66 and 68 are determined. This uses combining information from mirrors 50 and 52.

At each stage during bulging the position of the dot 64 under consideration is divided into two segments. The first segment $Z_1$ is calculated using the distance between the corresponding points recorded by the second mirror 52 (a'). The second segment $z_2$ is obtained using the distance between the corresponding points recorded using the first mirror 50 (c'). The calculation of the altitude, or height, of each dot 64 relies upon the geometry of the triangle 1

$$\sin(180°-2\phi)=a'/d$$

and triangle 2

$$\sin(180°-2\phi)=z_1/d$$

and triangle 3

$$\tan(180°-2\phi)=z_2/c'$$

thus $$z=z_1+z_2=-a'/\cos(2\phi)-c'\tan(2\phi)$$

Traditional analysis of bulge test results assume that the bulge, deformation, profile is circular. The bulge test measures the change in the dome segment height h and the chord length D, the projection of the arc length onto a plane perpendicular to the loading direction, see FIG. 10, thus enabling the radius R of the meridians curvature at the pole point to be obtained from the following equation $$R = \frac{(D/2)^2 + h^2}{2h}$$

Figure 10A:
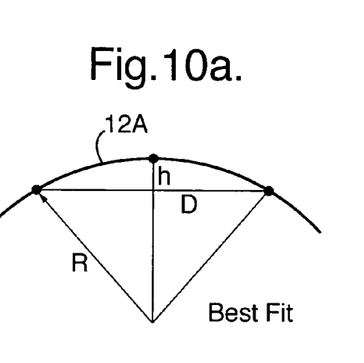
FIG. 10 is a chart showing calculation of radius of deformed article.
Figure 10B:
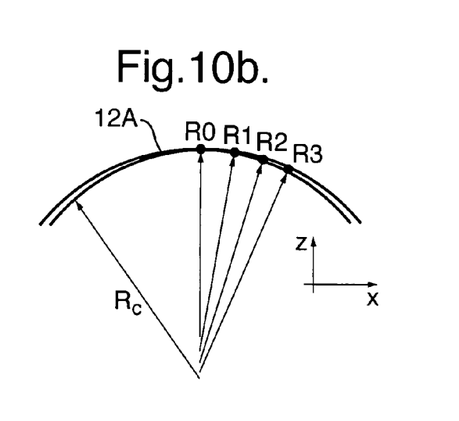

This procedure was followed to calculate the meridians arc lengths the relative height of the dome segments and the principal radii of curvature heights using pairs of dots 64, symmetrically arranged about the pole point 62, in either or both of the primary meridians 66 and 68 and the bulge dome was assumed to be orthosymmetric.

The mean thickness t of the dome segment may be calculated using a commonly used formula $$t=(D_0^2/(D^2+4h^2))t_0$$

Other more accurate formula may be used.

Stress and strain are calculated from the radius of curvature and the thickness at the pole point 62 of the deformed article 12A. In traditional bulge testing analysis the true in plane strain $\epsilon$ at the pole point 62 has been estimated using the change in chord length $$\epsilon=ln(D/D_0)$$

A formula traditionally employed in bulge testing analysis for a thin spherical shell expanded uniformly by internal pressure p, the membrane stress $\sigma$ is $$\sigma=pR/2t$$

Other more accurate formula may be used.

The processor 54 determines the chord length D, dome segment height h and radius R of the deformed article 12A between two points 64 arranged symmetrically about the pole point 62 of the deformed article. The processor 54 determines the thickness t of the deformed article 12A from the chord length D and dome height h of the deformed article 12A. The processor 54 determines the stress in the deformed article 12A from the pressure p applied and the original thickness of the article 12 and the radius R of the deformed article 12A.

Alternatively the means to measure the material properties of the article comprises two high-speed high resolution cameras arranged to produce a stereoscopic view of the article.

Although the camera has been described as a photographic camera it may be possible to use a digital camera in which case the signals supplied by the camera to the processor are digital and not analogue.

The present invention is able to provide multiracial tensile bulge testing of articles dynamically and enables better material characterisation during development and reduce number of large-scale tests. The present invention is applicable to the testing of materials for use in blade containment casings/systems of gas turbine engines and in particular for fan containment casings of turbofan gas turbine engines.

The article may be an actual article or a specimen.

We claim:

1. An apparatus for bulge testing an article comprising a pressure vessel arranged to define a chamber, the pressure vessel having a first aperture and a second aperture, means to pressurise the chamber, means to measure the deflection of the article, means to measure the pressure in the pressure vessel and means to determine material properties of the article using the measurements of pressure in the pressure vessel and the measurements of deflection of the article, a piston being arranged to move within the pressure vessel, the chamber being filled with a fluid, the means to pressurise the pressure vessel comprising a gun arranged to fire a projectile to strike the piston to produce a high pressure in the fluid in the chamber in the pressure vessel to deform the article, whereby in use the article being arranged over the first aperture in the pressure vessel to seal the pressure vessel wherein the means to measure the deflection of the article comprises at least one high-speed high-resolution camera and two mirrors arranged at different angles relative to the surface of the article in order to produce a stereoscopic view of the article, each mirror being arranged to focus on a respective portion of the image plane of the camera.

2. An apparatus as claimed in claim 1 comprising a clamping member having an aperture, the clamping member being arranged in use such that the aperture in the clamping member is aligned with the first aperture in a first end of the pressure vessel to clamp the article between the first end of the pressure vessel and the clamping member such that the article extends across the first aperture in the first end of the pressure vessel to seal the first end of the pressure vessel, the first end of the pressure vessel having a draw bead to deform the article and to prevent the article from being drawn into the pressure vessel.

3. An apparatus as claimed in claim 1 wherein the piston being arranged to seal a second end of the pressure vessel.

4. An apparatus as claimed in claim 1, wherein the gun including a barrel and the projectile being arranged to move within the barrel, an end of the barrel being secured to a second end of the pressure vessel and the second aperture in the second end of the pressure vessel being aligned with the barrel such that in use the projectile may strike the piston to produce a high pressure in the fluid in the pressure vessel to deform the article.

5. An apparatus as claimed in claim 1 wherein the pressure vessel has a minimum cross-sectional area at a position between a first end and a second end.

6. An apparatus as claimed in claim 1 wherein the gun is a gas gun.

7. An apparatus as claimed in claim 1 wherein the pressure vessel contains a liquid.

8. An apparatus as claimed in claim 7 wherein the pressure vessel contains an oil.

9. An apparatus as claimed in claim 1 wherein the means to measure the pressure comprises a high-speed high pressure gauge.

10. An apparatus as claimed in claim 1 wherein there are means to measure the velocity of the projectile before impact with the piston.

11. An apparatus as claimed in claim 10 wherein the means to measure the velocity comprises a plurality of light beams spaced apart along the length of the barrel, each light beam extends transversely across the barrel.

12. An apparatus as claimed in claim 1 wherein a first mirror is arranged at a predetermined angle and the angle of a second mirror is adjustable.

13. An apparatus as claimed in claim 12 wherein the first mirror is arranged at an angle of 45°.

14. An apparatus as claimed in claim 12 wherein the processor has means to determine the angle of the second mirror relative to the undeformed article.

15. An apparatus as claimed in claim 14 wherein the processor has means to determine the altitude of a polar point on the deformed article relative to the undeformed article from the determined angle of the second mirror.

16. An apparatus as claimed in claim 15 wherein the processor has means to determine the altitude of other points on the deformed article relative to the undeformed article from the determined angle for the second mirror.

17. An apparatus as claimed in claim 15 wherein the article has a grid of dots marked on the article, one of the dots being a polar point, means to determine the location of the polar point in the grid of dots in the two images of the article, means to determine the location of the dots in the grid of dots using the location of the polar point in the two images of the article and means to determine the deformation of the article using the change in the coordinates of the dots in the grid.

18. An apparatus as claimed in claim 17 comprising means to determine a chord length, a dome height and a radius of the deformed article between two dots arranged symmetrically about the polar point of the deformed article.

19. An apparatus as claimed in claim 18 comprising means to determine the thickness of the deformed article from the chord length and dome height of the deformed article.

20. An apparatus as claimed in claim 19 comprising means to determine the stress in the deformed article from the measurement of the pressure and the original thickness of the article and the radius of the deformed article.

21. A method of bulge testing an article comprising providing a pressure vessel arranged to define a chamber, the pressure vessel having a first aperture and a second aperture, a piston being arranged to move within the pressure vessel, the chamber being filled with a fluid, arranging the article over the first aperture in the pressure vessel to seal the pressure vessel, firing a projectile from a gun to strike the piston to produce a high pressure in the fluid in the chamber in the pressure vessel to deform the article, measuring the deflection of the article, measuring the pressure in the pressure vessel and determining material properties of the article using the measurements of pressure in the pressure vessel and the measurements of deflection of the article.

22. An apparatus for bulge testing an article comprising a pressure vessel arranged to define a chamber, the pressure vessel having a first aperture, means to pressurise the chamber, means to measure the deflection of the article, means to measure the pressure in the pressure vessel and means to determine material properties of the article using the measurements of pressure in the pressure vessel and the measurements of deflection of the article, wherein the means to measure the deflection of the article comprising two mirrors arranged at different angles relative to the surface of the article to produce a stereoscopic view of the article, each mirror being arranged to focus on a respective portion of the image plane of a camera.

23. A method of bulge testing an article comprising providing a pressure vessel arranged to define a chamber, the pressure vessel having a first aperture, arranging the article over the first aperture in the pressure vessel to seal the pressure vessel, pressurising the chamber in the pressure vessel to deform the article, measuring the deflection of the article, measuring the pressure in the pressure vessel and determining material properties of the article using the measurements of pressure in the pressure vessel and the measurements of deflection of the article, wherein the measuring of the deflection of the article comprising providing two mirrors arranged at different angles relative to the surface of the article to produce a stereoscopic view of the article and arranging each mirror to focus on a respective portion of the image plane of a camera.

24. A method as claimed in claim 23 comprising marking a grid of dots on the article, one of the dots being a polar point, determining the location of the polar point in the grid of dots in two images of the article, determining the location of the dots in the grid of dots using the location of the polar point in the two images of the article and determining the deformation of the article using the change in coordinates of the dots in the grid.

25. A method as claimed in claim 24 comprising determining a chord length, a dome height and a radius of the deformed article between two dots arranged symmetrically about the polar point of the deformed article.

26. A method as claimed in claims 25 comprising determining the thickness of the deformed article from the chord length and dome height of the deformed article.

27. A method as claimed in claim 26 comprising determining the stress in the deformed article from the measurement of the pressure and the original thickness of the article and the radius of the deformed article.

28. An apparatus for bulge testing an article comprising a pressure vessel arranged to define a chamber, the pressure vessel having a first aperture and a second aperture, means to pressurise the chamber, means to measure the deflection of the article, means to measure the pressure in the pressure vessel and means to determine material properties of the article using the measurements of pressure in the pressure vessel and the measurements of deflection of the article, a piston being arranged to move within the pressure vessel, the chamber being filled with a fluid, the means to pressurise the pressure vessel comprising a gun arranged to fire a projectile to strike the piston to produce a high pressure in the fluid in the chamber in the pressure vessel to deform the article, positioning means for holding the article being arranged over the first aperture in the pressure vessel to seal the pressure vessel.

* * * * *